United States Patent
Dorn et al.

(10) Patent No.: US 9,901,469 B2
(45) Date of Patent: *Feb. 27, 2018

(54) HAND-HELD ACTUATOR DEVICE

(71) Applicant: C. R. Bard, Inc., Tempe, AZ (US)

(72) Inventors: Jurgen Dorn, Neulussheim (DE);
Martin Wubbeling, Mannheim (DE);
Michael Vogel, Karlsruhe (DE)

(73) Assignee: C. R. Bard, Inc., Tempe, AZ (US)

( * ) Notice: Subject to any disclaimer, the term of this patent is extended or adjusted under 35 U.S.C. 154(b) by 273 days.

This patent is subject to a terminal disclaimer.

(21) Appl. No.: 14/793,669

(22) Filed: Jul. 7, 2015

(65) Prior Publication Data
US 2015/0305900 A1  Oct. 29, 2015

Related U.S. Application Data

(62) Division of application No. 12/376,670, filed as application No. PCT/EP2007/058205 on Aug. 7, 2007, now Pat. No. 9,078,779.

(30) Foreign Application Priority Data

Aug. 7, 2006 (GB) .................................. 0615658.2

(51) Int. Cl.
*A61F 2/06* (2013.01)
*A61F 2/95* (2013.01)
*A61F 2/966* (2013.01)
*A61F 2/962* (2013.01)
*A61M 25/01* (2006.01)
*A61F 2/92* (2013.01)

(52) U.S. Cl.
CPC ................. *A61F 2/95* (2013.01); *A61F 2/962* (2013.01); *A61F 2/966* (2013.01); *A61F 2/92* (2013.01); *A61F 2002/9517* (2013.01); *A61M 25/0147* (2013.01); *A61M 2025/015* (2013.01)

(58) Field of Classification Search
CPC .. A61F 2/95; A61F 2/962; A61F 2/966; A61F 2002/9517; A61F 2/92; A61M 2025/015; A61M 25/0147
See application file for complete search history.

(56) References Cited

U.S. PATENT DOCUMENTS

| | | | | |
|---|---|---|---|---|
| 6,315,794 B1* | 11/2001 | Richter | ...................... | A61F 2/91 623/1.34 |
| 2003/0163193 A1* | 8/2003 | Widenhouse | ........... | A61F 2/966 623/1.12 |
| 2006/0093643 A1* | 5/2006 | Stenzel | ...................... | A61F 2/82 424/423 |
| 2007/0061007 A1* | 3/2007 | Nolting | ...................... | A61F 2/91 623/1.42 |
| 2008/0140175 A1* | 6/2008 | Boucher | ................. | A61F 2/966 623/1.11 |
| 2010/0145429 A1* | 6/2010 | Dhoke | ...................... | A61F 2/95 623/1.11 |

* cited by examiner

*Primary Examiner* — Richard Louis

(57) ABSTRACT

A hand-held actuator device for releasing into the body from a delivery system a medical prosthesis, like a stent, comprising a frame that acts as a housing, a reel for receiving a wire, a manually operable slider mounted to the frame and a one-way connection between the slider and the reel. Actuating the slider causes the reel to wind up the wire and release the medical prosthesis.

15 Claims, 3 Drawing Sheets

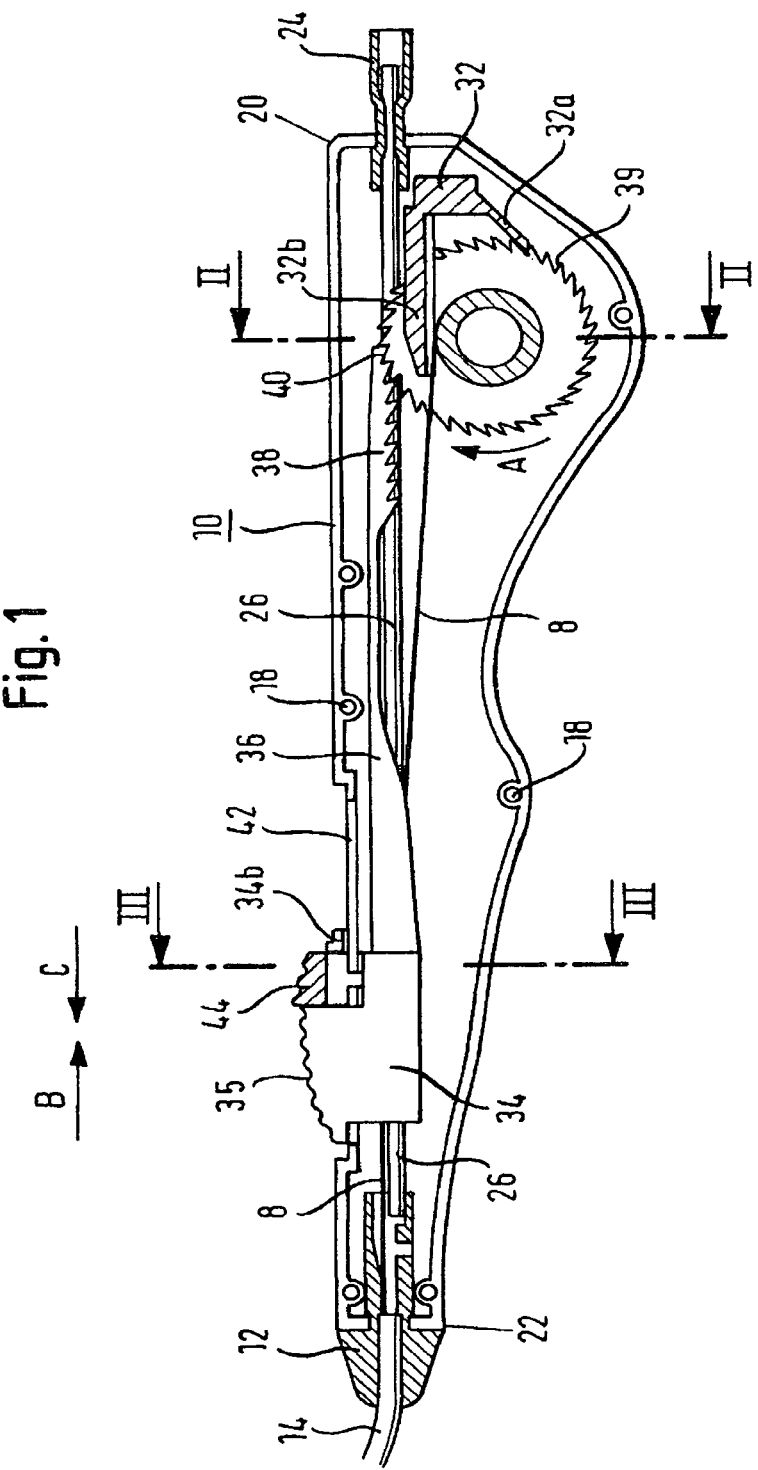

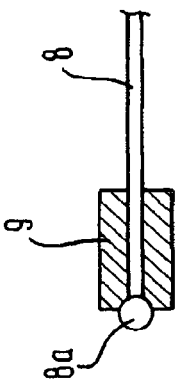
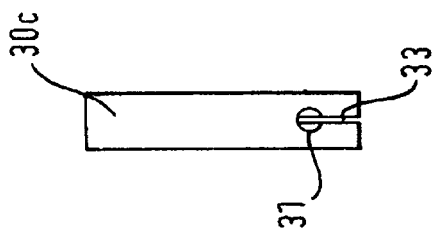
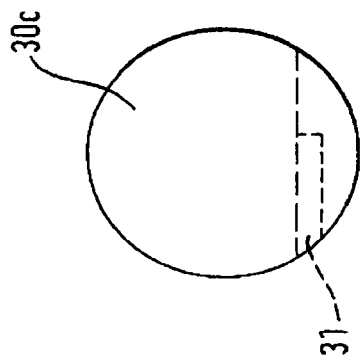
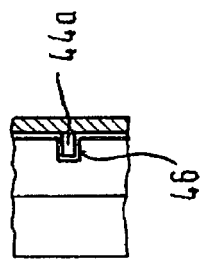

HAND-HELD ACTUATOR DEVICE

PRIORITY

This application is a divisional of U.S. application Ser. No. 12/376,670, filed Feb. 6, 2009, now U.S. Pat. No. 9,078,779, which is a U.S. national stage application under 35 U.S.C. § 371 of International Application No. PCT/EP2007/058205, filed Aug. 7, 2007, claiming priority to Great Britain Patent Application No. 0615658.2, filed Aug. 7, 2006, each of which is incorporated by reference in its entirety into this application.

FIELD OF THE INVENTION

The present invention relates generally to a catheter based system for treating a remote location within a patient and more particularly to the hand-held actuator devices of stent delivery systems.

BACKGROUND

A delivery system for a self-expanding stent usually has the stent distally adjacent to a tube, both within a sleeve at the distal end of a catheter. To deliver the stent, the sleeve has to be pulled back while the tube holds the stent from moving back with the sleeve. Therefore, the tube is placed adjacent to the stent and acts as a barrier and restrains the stent from moving while the sleeve is pulled back.

WO 02/087470 discloses a hand device for a catheter stent delivering system. The hand device can be operated one-handed to ease the operation with such a device. The main function such devices have to include are:
1) to pull back the sleeve, for example by pulling a wire which is connected to the proximal end of the outer sleeve;
2) to restrain simultaneously the inner tube from being pulled back together with the sleeve; and
3) to provide a visual signal of how much length of the sleeve has already been pulled back The restraint function can be performed by a hub that is mounted within the hand-held actuator and itself receives the proximal end of the tube. To pull the wire, in WO 02/087470 is provided an index-finger-triggering-system, which causes a mechanical apparatus within the device to pull in the wire and draw the proximal end of the sleeve into the housing of the hand unit. A disadvantage of the index-finger-triggering-system is that it is a pistol-like device and the impression it gives to the operator, of direct tactile feedback about the progress of stent release, some operators might find unconvincing. Furthermore, the maximum length of wire, which can be reeled in by successive squeezes of the trigger, is defined by the length of the track in the hand unit along which the proximal end of the sleeve advances proximally, rendering it incapable of releasing a self-expanding stent which is longer than the track.

EP 1 299 050 discloses a thumb-actuating-screwing-system, but this has all disadvantages of the index-finger-triggering-system. In addition the thumb has to be lifted between every turn of the screw, which makes the control of the pull-mechanism less comfortable.

Both of the above identified systems have a component protruding from the housing of the hand unit, which moves proximally through the device with the catheter being withdrawn, and so acts as a distance indicator. When the operator starts coiling-up the wire, the indicator moves and the operator and his or her assistants can judge the extent of the progressive stent release from the distance the indicator has travelled proximally along the length of the housing of the hand unit.

Stents are getting longer (e.g. in a leg the stent can be about 30 cm). It is one object of the present invention to provide a hand-held actuator for release of a self-expanding stent with a length longer than can be handled by the known hand-held actuators.

Generally, the present invention aims to improve on the performance of the devices of WO 02/087470 and EP 1 299 056, in the respects mentioned above.

SUMMARY OF THE INVENTION

According to the present invention there is provided a device for releasing into the body from a delivery system a medical prosthesis, like a stent, of the form discussed herein. Optional or preferred features of the invention are mentioned in the claims.

In a first preferred embodiment, the device comprises a frame, which can be moulded of plastic and acts as housing. At its distal end a hub is provided, which acts as an abutment system for the tube. A slider is connected in a one-way connection to a reel, which is caused to rotate by a pull stroke of the slider. The reel winds a portion of a length of the wire by every pull stroke and holds the position by every return stroke. A detent restrains the reel from moving during a return stroke, so the reel is urged to move in only one direction.

In a second embodiment the slider is formed as a thumb pad and has a carriage portion on his flanks. It slides on a track, which is defined by the frame. In a rest position, the slider is restrained from sliding by a slider release element, which is located within the thumb pad and which prevents the wire inadvertently being pulled proximally. In the restraining initial position the slider release element protrudes from the carriage portion of the slider. The slider release element can be urged in a second release position, which allows the slider to move free on the track.

Particularly when the slider slides on a track in a direction parallel to the axis of the catheter, the operator has the sensation that the thumb pad delivers useful tactile feedback about what happening at the distal end of the catheter, where the stent is being released.

In a third embodiment, the one-way connection comprises teeth on a elongation of the slider element and co-operating teeth on a rotatory element which is operatively connected to the reel. The one-way connection could be located between the teeth of the slider and the rotatory element. In this case the teeth are formed such that they engage in one way and slip over in the reverse direction. Such embodiment can enhance the sensation of tactile feedback to the operator, through the wire and reel to the slider.

In another embodiment the detent is formed as a pawl to engage with the reel or, more specifically, with the teeth of the rotatory element, to restrain it from moving in the reverse direction. This finger preferably points in the rotatory direction of the wheel. In another construction of the detent a finger engages with the wire such that the finger pushes the wire onto the reel. In this case the restraining force comes from the resilience of the wire in addition to the friction between the wire and the finger. In a further embodiment, the detent comprises both the pawl and the finger. Embodiments that include such a pawl can provide audible feedback to the operator (and others working with the operator}, in the form of clicking sounds, about the rate of progress of the stent release operation.

These embodiments can be used with stent delivery catheters, both 'over the wire' and 'rapid exchange'. They can be used regardless whether it is the inner or the outer element of the co-axial shaft of the catheter which is proximally withdrawn relative to the other to release the stent. A catheter system which employs the inner of two co-axial shaft elements to pull proximally back a sheath that surrounds a self-expanding stent at the distal end of the catheter is called a 'pull-wire' stent delivery catheter. Such a pull wire system is useful for delivering ultra-long stents, because the reel can accommodate a length of the pull wire longer than the stent, however long the stent is.

The described embodiments need very few mechanical elements. This avoids unnecessary waste and minimizes assembly time and weight of the device. Furthermore, with the pull wire of the catheter system connected directly to the reel there is no limit to the length of wire that can be withdrawn proximally. With relatively short stents, when placement in the body is delicate, the slider can still act as an indicator of stent release progress, and how much of the stent length is still to be released.

The design of the device can be formed ergonomically such it is comfortable for every hand size of any operator. In addition, the thumb of the gripping hand falls naturally on the thumb pad of the slider.

Recapitulating some advantages of the present invention over the above mentioned prior art systems are:
better tactile feedback about the stent delivery progress
no limitation of the stent length, with simultaneous visual information about the stent delivery progress stepless wire-pulling and audible feedback of the operation progress
improved handling through ergonomic design reduced number of mechanical components

BRIEF DESCRIPTION OF THE FIGURES

FIG. 1 shows a longitudinal section of a preferred embodiment;
FIG. 4 is a side view to show a borehole and a groove in the cylindrical drum of the reel;
FIG. 5 is a front view of the drum of FIG. 4;
FIG. 6 is a side view of an end of the wire;
and
FIG. 7 is a section along the line IV-IV in FIG. 3 seen from above.

DETAILED DESCRIPTION

Figure 3:
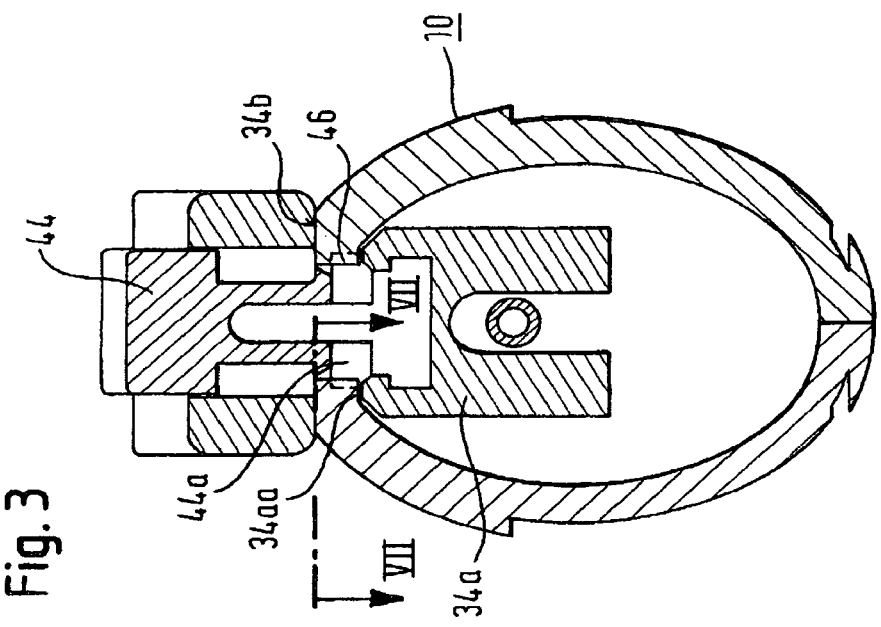
FIG. 3 shows a transverse section along the line III-III in FIG. 1.

The invention can be embodied in a device for pulling a wire 8 out of a tube 14 and which can be activated, preferably with only one hand.

The drawings show a preferred embodiment of the invention. FIG. 1 shows one half of a molded housing 10 which serves as a frame for mounting the various components of the device, and has a proximal end 20 and a distal end 22. The housing is almost symmetric and the two half housing parts are fixed together with screws 18 (or something similar like rivets or plugs) at defined places. A portion of each half of the housing is covered with a rubber material (not shown). This increases the grip and eases the handling of the device.

A first hub 12 is fixed at the distal end 22 of the housing, acting as an abutment and bearing element for guiding the tube 14 to the housing 10. The tube 14 terminates in the hub 12, so that a wire 8 can be pulled out of the tube. The hub 12 acts as an abutment element and stops the tube 14 from being pulled into the housing 10. Through this abutment element extends an inner tube 26 to a second hub 24 at the proximal end 20 of the housing 10. The second hub 24 provides a female luer connector to engage a corresponding male luer, for flushing liquid for the lumen of the tube 14.

A reel 30 is provided to take up the wire 8 and is preferably near the proximal end 20 of the housing 10 rotatably mounted in the housing. The reel is flanked by two large discs 30a, 30b, spaced apart by a cylindrical drum surface 30c of the reel for the wire. Both of the discs have a toothed circumferential surface to provide a ratchet element (see FIG. 3). In other embodiments there could be only one smooth wheel and one ratchet wheel instead of both wheels being ratchet wheels.

The reel coils up the wire when it rotates in the direction of arrow A and would release the wire if it were able to rotate in the opposite direction.

To attach the wire 8 to the reel 30 there is provided a special ball-end on the wire and 8 a borehole in the drum With reference to FIGS. 4, 5 and 6 a borehole 31 is provided in the cylindrical drum 30c. The borehole 31 leads from the surface of the cylindrical drum 30c, in a direction transverse to the rotatory axis into the drum 30c, to an abutment surface 31c. A groove 33 co-axial with the borehole 31 links the borehole with the surface of the drum.

The end of the wire 8 carries a sleeve 9 and a ball Ba, welded to the end of the wire 8. The wire B is put with the free end into the sleeve 9 and the ball Sa stops the wire 8 from sliding through the sleeve 9. Another way fixing the 8 sleeve 9 to the wire 8 could be to weld the ball Sa on the wire 8 after putting it through the sleeve 9.

In another embodiment the wire and the sleeve are pressed together such the sleeve 9 is fixed on the wire.

The wire 8 is threaded into the groove 33 and the sleeve 9 is advanced into the borehole 31. Pulling the wire urges the sleeve to slide into the first borehole 31a, which has a diameter slightly bigger than the sleeve 9, and blocks the wire from being pulled further.

To avoid releasing a coiled up wire, a backstroke-stopper 32 (otherwise called 'detent') is provided near the reel 30. In the preferred embodiment the stopper has two fingers. The first is a detent 32a which functions as a pawl by engaging the teeth of the ratchets 30a and/or 30b. The teeth of the ratchets are so shaped that the finger 32a does not prevent the ratchet from rotating in direction A, but stops the reel rotating in the other direction by engaging into a gap between adjacent teeth.

Figure 2:
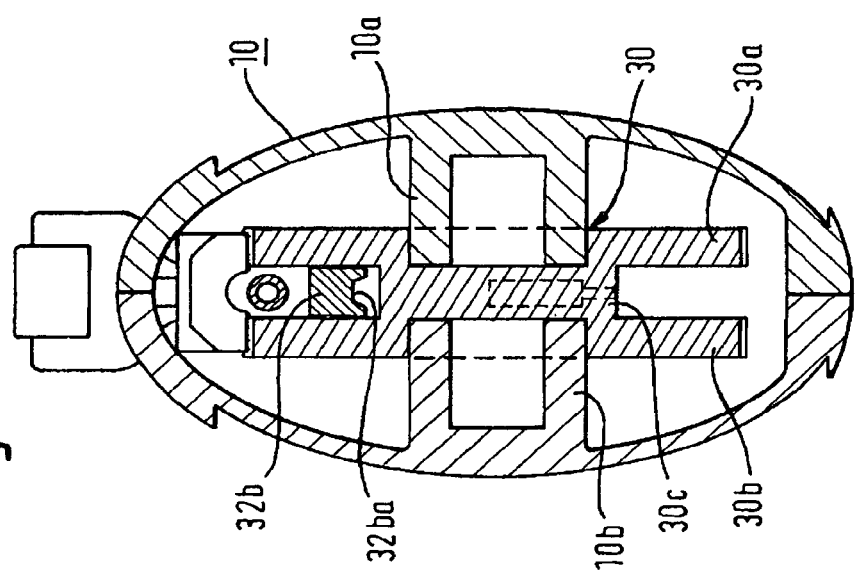
FIG. 2 shows a transverse section along the line II-II in FIG. 1.

The second finger 32b serves to press the already coiled wire towards the rotational axis of the reel. The wire is springy so it tends to straighten when it can and so will tend to unroll from the reel. The second finger prevents this happening. Preferably the second finger 32b has a recess 32ba (as shown in FIG. 2) facing the wire to receive the wire 8. When the second finger 32b presses down the wire 8, there is friction between the wire and the finger. This friction, together with the resilience of the wire, can act as a brake in the rotation of the reel. Indeed, such a brake can render any ratchet and pawl superfluous. One advantage of a brake over a ratchet in that one can achieve a stepless pulling of the wire 8.

To urge the reel to rotate to wind in the wire 8, in direction A, a slider 34 is provided. This slider has a thumb pad 35 and is operably connected to the reel by its elongate extension 36 that has a toothed straight ratchet profile 38 at its end remote from the thumb pad. The toothed straight profile 38 and the toothed ratchet on the periphery of each of the reel discs 30*a*, 30*b* provide a one-way-connection 40 in which the reel rotates when the slider is moved in the direction of arrow B. When the discs are so urged to rotate, the drum 30*c* between the two discs is also rotating and the wire is coiled up. When the slider is urged in the reverse direction, arrow C, the teeth of the straight ratchet slide over the teeth of the discs (see 40). In another embodiment the straight ratchet and the discs may be fixedly connected such that both move together, in both directions. A one-way bearing in the hub of the reel allows the wire take-up reel to rotate in the direction of arrow A, but not in direction of arrow B. Of course the movement directions of the particular elements are changeable at will. For example, if the wire coils up anti-clockwise on the reel, rather than clockwise, each would be arranged the other way.

The slider slides on a track 42, defined by the housing 10. The slider includes a slider release element 44, that is moveable between a relaxed gripping disposition and a pushed down release disposition. The release element, when not pushed down, is formed such that a detent 44*a* of the slider release element is blocked by a recess 46 the housing (as shown in FIG. 7). This restrains inadvertent sliding of the slider. When the slider is to be moved, the slider release element is first pushed down until the detent engages the corresponding locker element 34*aa* on the inner part of the slider 34*a* and is being held down. As a result the slider 34 is released from the recess 46 in the housing and is free to move along the track 42.

In another embodiment there could be provided a distance scale (not shown) next to the sliding track advancing the distance indication by the slider.

In another embodiment, there is provided a spring (not shown) in the housing 10, which is connected to the slider and urges the slider to slide back into the first pull back position automatically.

As soon as the slider release element 44 is no longer pushed down, it moves up again as a result of its resilience and the ramps 44*a* and 34*aa*, once again to restrain slider movement.

In the present embodiment all device members (reel, housing, slider, head, hub and stopper) are molded from plastics. In other embodiments components can be provided as separate individual parts (e.g. the reel in one smooth, smaller wheel and two ratchets). These parts can be formed of various materials (e.g. metal, different kinds of plastics) and assembled (by screwing, plugging, welding, riveting) as desired.

What is claimed is:

1. A device comprising:
a frame comprising a track;
a reel mounted to the frame;
a detent mounted on the frame and that engages the reel;
a slider mounted to the frame and adapted for a backward stroke and a forward stroke and further comprising a carriage that slides along the track and a reversible slider lock that locks the slider to the track;
a connection that engages the slider and the reel during the backward stroke, configured to wind some of a wire onto the reel, and that disengages the slider and the reel during the forward stroke.

2. The device of claim 1 wherein the lock sits within a thumb pad that protrudes from the carriage.

3. The device of claim 2 further comprising a ruler lying adjacent the track.

4. The device of claim 3 wherein the connection comprises teeth on the slider and cooperating teeth on the reel or on an element connected to the reel.

5. The device of claim 4 wherein the teeth engage during the backward stroke and slip over each other during the forward stroke.

6. The device of claim 5 wherein the detent comprises at least one resilient finger.

7. The device of claim 6 wherein the detent comprises a pawl that engages the reel.

8. The device of claim 7 wherein the wire connects to the reel.

9. The device of claim 8 further comprising: a catheter having a proximal end joined to a distal end of the frame; a sheath disposed coaxially inside at least the distal end of the catheter and attached to the wire; and a self-expanding stent mounted in the sheath.

10. A device comprising:
a frame comprising a track;
a reel mounted to the frame;
a detent mounted on the frame and that engages the reel;
a slider mounted to the frame and adapted for a backward stroke and a forward stroke and further comprising a carriage that slides along the track;
a connection that engages the slider and the reel during the backward stroke, configured to wind some of a wire onto the reel, and that disengages the slider and the reel during the forward stroke,
wherein the detent comprises at least one resilient finger.

11. A device comprising:
a frame comprising a track;
a reel mounted to the frame;
a detent mounted on the frame and that engages the reel;
a slider mounted to the frame and adapted for a backward stroke and a forward stroke and further comprising a carriage that slides along the track;
a connection that engages the slider and the reel during the backward stroke, configured to wind some of a wire onto the reel, and that disengages the slider and the reel during the forward stroke,
wherein the detent pushes down the wire on the reel.

12. The device of claim 11 wherein the force to restrain the reel from rotation during the forward stroke comes from the resilience of the wire in addition to the friction between the wire and the detent.

13. The device of claim 12 wherein the detent comprises a pawl that engages the reel.

14. The device of claim 13 wherein the wire connects to the reel.

15. The device of claim 14 further comprising: a catheter having a proximal end joined to a distal end of the frame; a sheath disposed coaxially inside at least the distal end of the catheter and attached to the wire; and a self-expanding stent mounted in the sheath.

* * * * *